United States Patent [19]

Wakizaka et al.

[11] 4,304,651
[45] Dec. 8, 1981

[54] SOLID POLE OXYGEN SENSOR

[75] Inventors: Hiroshi Wakizaka, Toyota; Hiroshi Shinohara, Okazaki; Yasuhiro Otsuka; Shinichi Matsumoto, both of Toyota, all of Japan

[73] Assignee: Toyota Jidosha Kogyo Kabushiki Kaisha, Aichi, Japan

[21] Appl. No.: 103,472

[22] Filed: Dec. 14, 1979

[30] Foreign Application Priority Data

Jun. 27, 1979 [JP] Japan .................................. 54/81094

[51] Int. Cl.³ ............................................. G01N 27/58
[52] U.S. Cl. ................................................ 204/195 S
[58] Field of Search ................................. 204/1S, 195 S

[56] References Cited

U.S. PATENT DOCUMENTS

| | | | |
|---|---|---|---|
| 3,334,039 | 8/1967 | Vlasak | 204/195 P |
| 3,642,599 | 2/1972 | Franz | 204/195 S |
| 3,719,574 | 3/1973 | Richardson | 204/195 S |
| 3,785,948 | 1/1974 | Hitchman et al. | 204/195 P |
| 3,871,981 | 3/1975 | Flais et al. | 204/195 S |
| 3,883,408 | 5/1975 | Kim et al. | 204/195 S |
| 3,915,830 | 10/1975 | Isenberg | 204/195 S |
| 4,035,277 | 7/1977 | Hennessy et al. | 204/195 S |
| 4,045,319 | 8/1977 | Deportes et al. | 204/195 S |
| 4,128,469 | 12/1978 | Rohr et al. | 204/195 S |
| 4,177,125 | 12/1979 | Barnabe | 204/195 S |
| 4,208,265 | 6/1980 | Hori et al. | 204/195 S |
| 4,209,378 | 6/1980 | Schinohara et al. | 204/195 S |

Primary Examiner—G. L. Kaplan
Attorney, Agent, or Firm—Stevens, Davis, Miller & Mosher

[57] ABSTRACT

A solid pole oxygen sensor having a solid pole, in which one end of a lead wire of platinum or platinum rhodium is buried, tightly covered by a solid electrolyte and pressure-molded into a circular plate, which is dried and then fired in a reducing atmosphere. The surface of a sintered mass thus obtained is plated or baked to form a platinum electrode, and the oxygen sensor element thus obtained is secured by a bonding agent to the tip of a cylindrical ceramic insulator having electroconductive zones to be connected to the platinum electrode in such a manner that the circular face of the circular plate-shaped oxygen sensor element is in contact with the tip surface of the cylindrical ceramic insulator.

11 Claims, 13 Drawing Figures

FIG. 3A
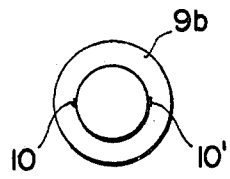
FIG. 3B
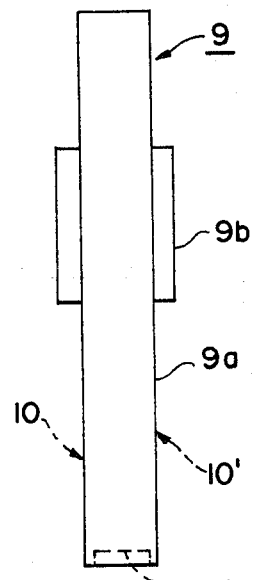
FIG. 3C
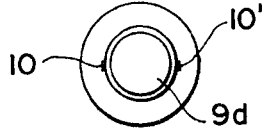
FIG. 4A
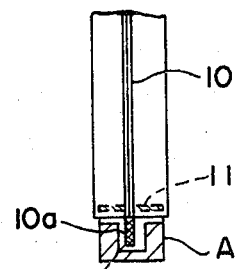
FIG. 4B
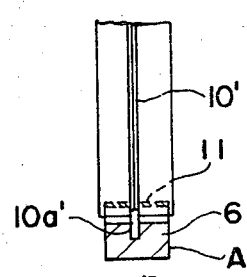
FIG. 4C
FIG. 4D
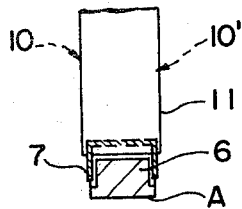
FIG. 4E
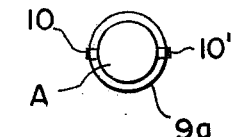

SOLID POLE OXYGEN SENSOR

CROSS-REFERENCE TO RELATED APPLICATION

This application shows, describes and claims a solid pole oxygen sensor and its manufacturing process as does commonly assigned U.S. patent application Ser. No. 091,883 filed Nov. 7, 1979 by Hiroshi Wakizaka et al and entitled "SINGLE POLE OXYGEN SENSOR AND ITS MANUFACTURING PROCESS."

BACKGROUND OF THE INVENTION

1. Field of the Invention

The present invention relates to a solid pole oxygen sensor and its manufacturing process.

The oxygen sensor is a means of measuring the equilibrium oxygen partial pressure in, say, the exhaust gas from an automotive engine.

2. Description of the Prior Art

Prior art oxygen sensors have a solid electrolyte vessel made of a solid electrolyte such as zirconia stabilized by yttrium oxide, etc. On the outside and inside surfaces of this vessel are formed internal and external electrode layers of platinum or platinum alloy film. The vessel is filled with an internal reference substance, i.e., a gas with a constant oxygen content like air or a solid with a constant equilibrium oxygen partial pressure such as a mixed powder of metal-metal oxide.

The ratio between the equilibrium oxygen partial pressures of a gas to be measured, which comes into contact with the external electrode layer and the internal reference substance which is in contact with the internal electrode layer is converted to an electromotive force, by which the equilibrium oxygen partial pressure in the gas to be measured can be determined. As the internal reference substance in said oxygen sensor, a gas or a solid is available. Functionally and structurally, the solid has been found to be better than the gas, when it is to serve as part of automotive equipment.

However, the conventional solid pole oxygen sensor, including a solid electrolyte vessel, which involves a difficult step of calcining of the vessel or high-temperature firing for manufacture, is complicated in structure and unfit for miniaturization. Moreover, it is difficult to take out of the vessel the potential of the internal electrode layer in the solid electrolyte vessel.

BRIEF SUMMARY OF THE INVENTION

The primary object of the present invention is to provide a solid pole oxygen sensor which is simplified in structure and fit for miniaturization.

Another object of the present invention is to provide a solid pole oxygen sensor which maintains excellent performance even after long service due to the fact that a circular plate-like oxygen sensor element is tightly joined with an insulator.

A further object of the present invention is to provide a solid pole oxygen sensor and producing process thereof characterized in that a solid pole in which one end of a lead wire of Pt or Pt-Rh is buried is tightly covered by a solid electrolyte and press-molded into a circular plate; the thus obtained molding is dried and sintered and then a Pt-electrode is formed on the surface of the sintered product to produce an oxygen sensor element. The sensor element is joined to the tip of an approximately cylindrical ceramic insulator by means of a bonding agent in such a manner that the tip surface of the insulator is in contact with the circular face of the circular plate-like oxygen sensor element.

BRIEF DESCRIPTION OF THE ATTACHED DRAWINGS

FIG. 3a is a top plan view of the ceramic insulator;

FIG. 3b is a front elevational view of FIG. 3a;

FIG. 3c is a bottom plan view of FIG. 3b;

FIGS. 4a and 4b are enlarged side views showing the joint between the sensor element A and the insulator as viewed from the positive side and negative auxiliary electrodes;

FIG. 4c is a bottom plan view of FIGS. 4a and 4b;

FIG. 4d is a front elevational view of FIGS. 4a and 4b;

FIG. 4e is a bottom plan view of FIG. 4d;

DETAILED DESCRIPTION OF THE INVENTION

Figure 1:
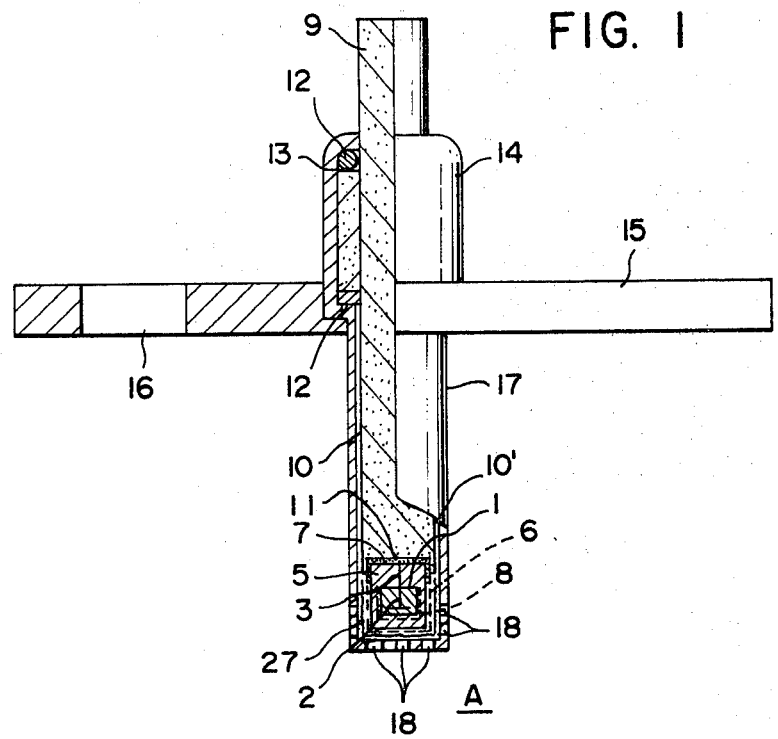
FIG. 1 is a side view partly in section showing the structure of a solid pole oxygen sensor according to the present invention.
Figure 2:
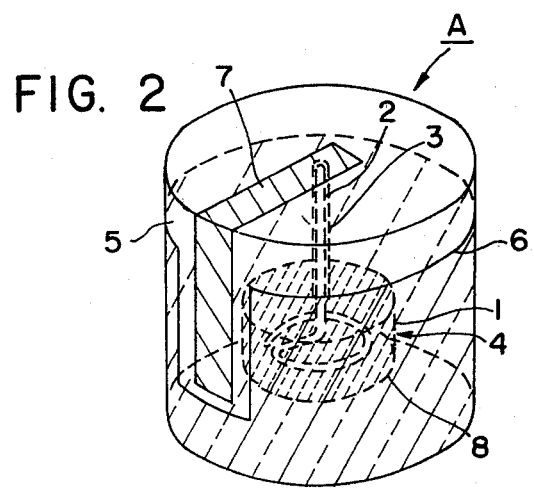
FIG. 2 is a perspective view of the oxygen sensor element.

As illustrated in FIG. 1, the oxygen sensor according to the present invention includes a lead wire 2, having a diameter of 0.05-0.5 mm$\phi$ and made of Pt or Pt-Rh, one end of which is buried in a solid pole 1. The surface of the unburied portion of the lead wire 2 is coated with a sealing agent 3 as shown in FIG. 2. An internal negative electrode (minus side) 8 is formed on the surface of said solid pole 1, thereby constituting a solid electrode 4. The solid electrode 4 is wrapped or encased in a solid electrolyte 5, which is molded into a circular plate under a pressure of 600-2000 Kg/cm$^2$, and dried. The molded circular plate is then fired at about 1350°-1500° C. in a reducing atmosphere. The sintered mass thus obtained has a positive electrode 6 and a negative (auxiliary) electrode 7 formed on its surface by means of plating or baking to form an oxygen sensor element A. The oxygen sensor element A is fitted or secured by means of a bonding agent 11, to the tip of an approximately cylindrical ceramic insulator 9 having electroconductive zones 10, 10' provided longitudinally, which are respectively connected to the positive electrode 6 and the negative auxiliary electrode 7 in such a manner that the tip is in contact with the circular surface of the oxygen sensor element A. Then, the surface of the oxygen sensor element is provided with a spinel coating layer 27 of MgAl$_2$O$_4$ (50-150$\mu$) which is formed by plasma spray coating. Finally, the assembly thus obtained is mounted on a holder consisting of the housing 14, the flange 15 having a fitting hole 16 therein and a protective cover 17 having ventilation holes 18 therein. As shown in FIG. 1, a metal packing 12 and a filler 13 are positioned between the ceramic insulator 9 and the housing 14.

The solid pole 1 in the oxygen sensor element A according to the present invention is made of a metal and its oxide, for instance Co/CoO, V/VO, Fe/FeO, etc. to which other additives such as an anti-sinter agent, a foaming agent and the like, are added in adequate appropriate quantities.

As the anti-sinter agent, the same substance as the solid electrolyte 5, for instance, $ZrO_2$ added or stabilized with $Y_2O_3$ is preferable. As the foaming agent, a substance which sublimates at a low temperature of less than 100° C. is available. When Fe/FeO is utilized as the solid pole 1, the composition will be: Fe (carbonium decomposed from powder)—45% by weight; 5.5 mol % $Y_2O_3$-$ZrO_2$—10% by weight; and the foaming agent will consist of $NH_4HCO_3$—45% by weight.

Further, for the purpose of improving the activity of the solid pole, a small volume of platinum black, say, 20% by weight, will be added as the activating agent.

The lead wire 2 should be fine but not so fine as to be liable to snap or break apart. The diameter of the lead wire may be 0.05–0.5 mm$\phi$, and more desirably 0.05–0.2 mm$\phi$. If the wire diameter is large, the surface area will increase, resulting in a poor sinterability of the surrounding solid electrolyte. If the wire diameter is too small, the sinterability will be kept but the wire will become liable to snap or break apart.

The lead wire 2 is made of Pt or Pt-Rh. When the lead wire 2 is made of Pt-Rh, it is desirable that an additional amount of Rh to Pt be provided or for example 10–30% by weight with the optimum value being 15–25% by weight. At less than 10% by weight, the heat resistance drops, causing the wire to snap or break apart. At more than 35% by weight, the durability increases but the ductility and flexibility of the wire deteriorate, resulting in inadequate workability.

The sealing agent 3 to be applied around the lead wire 2 buried in the solid pole 1 or around the projection of the lead wire 2 is an electroconductive metal, such, as Pt or a Pt-Rh alloy and an organic binder. For instance, as the sealing agent, a paste-like one may be used such that an organic binder, e.g. ethylcellulose + butyl carbitol acetate (BCA) or nitrocellulose + butyl acetate is blended with more than 15% by weight, desirably 15–20% by weight, of Pt. The organic binder employed is desirably one based on nitrocellulose, which is easier to eliminate through heating.

The conventional solid pole oxygen sensor is sealed with a glass sealant, which can leak and perform inadequately in a high-temperature durability test.

The sealant used in the present invention is an electroconductive paste, such as metallic paste, which, together with Pt metallization, produces excellent sealing and performs well with no gas leakage.

The solid electrolyte 5 is $ZrO_2$ stabilized with 4–10 mol % of $Y_2O_3$. A partially stabilized $ZrO_2$ is desirable from the standpoint of resistance to heat shock and $ZrO_2$ with a low mol % content of $Y_2O_3$ is desirable for the purpose of low-temperature firing. The anti-sinter agent, which is listed above, to be added to the solid pole is desirably the same material as the solid electrolyte.

For molding of the element A, for instance, by using a hand-press, the solid electrode 4 tightly covered by a solid electrolyte is press-molded into a circular plate in a specified mold under a molding pressure of 600–2000 Kg/cm², preferably 600–1200 Kg/cm². Under a molding pressure of more than 2000 Kg/cm², removal of air out of the molded product is insufficient. As a result, air bubbles are left in the sintered mass and the quality of the finished product is poor.

The profile of the sensor element A may also be molded into a small cylinder shape having a height which is a little greater than that of the circular plate.

The circular plate-like sensor element A thus obtained is dried at 200° C. in the atmosphere for 15–30 minutes to drive the organic binder out of the sealing agent. The drying temperature in the oxidizing atmosphere is 300° C. at the most and the drying time will naturally be shortened under a reduced pressure.

Maximum pressure reduction is 100 mmHg. Further reduction will not be effective, because it causes a change in the molded product.

Firing is carried out at a high temperature of 1350°–1500° C. for 2–3 hours in an electric furnace in a reducing atmosphere of inert gas such as Ar or $N_2$ with a small amount (0.5–2% by volume) of a reducing gas such as $H_2$. Although as a general rule, the higher the firing temperature the better, when the prevention of sintering, particle growth of the solid pole and the deterioration of lead wire is considered, the firing temperature is desirable lower than the sintering temperature of the solid pole and thus the above-mentioned range is found optimum. It is particularly necessary that the temperature be one at which a strong sintering of the solid pole does not take place or one at which the metal of the solid pole does not melt. The sintering time depends on the kind of solid electrolyte employed and the sintering treatment is carried out until the water absorption in the sintered means becomes 0% (as measured according to JIS R 2205). Since it is not desirable for sinterability to raise the temperature in a short time, i.e., very quickly, the adequate rate of temperature elevation will be 100°–300° C./hr.

The positive electrode 6 and the negative auxiliary electrode 7 on the surface of the solid electrolyte are made of Pt or Pt and another element of the platinum family. They can be made by Pt plating, Pt paste application baking, chloroplatinic acid-baking, Pt printing, ion plating, etc. The plating method is recommended. The negative (solid pole) electrode 8 around the solid pole 4 should be made of the same material as the sealing agent.

Examples of electrode constitution are given below:

| Pretreatment | etching (hydrofluric acid) | 30 min. |
|---|---|---|
| | ultrasonic washing | 3 min. |
| | immersion in platinum solution | 10 min. |
| | drying at room temperature | 8 hr. |
| Surface reduction | (by commercial reducing agent) | 10 min. |
| Pt chemical plating | surface resistance | 5 $\Omega$ |
| Pt electric plating | less than 1 $\Omega$ for film thickness 1 $\mu$ | |

Chloroplatinic acid baking:

The element is dipped into a solution of chloroplatinic acid in butylcarbitol, taken out of it and then dried, the dipdry process is repeated until the surface resistance reaches about 1$\Omega$.

Platinum paste coating and baking:

The surface of the element, after being pre-treated (degreased), is evenly coated with a commercially available Pt paste. After drying, the element is baked in the atmosphere at 950° C. for 10 minutes.

The element A for the solid pole oxygen sensor according to the present invention is constituted as follows: As illustrated in FIG. 2, the tip of the lead wire 2 to be buried in the solid pole 1 is formed into a substantially circular configuration to suit the configuration of the solid pole 1. The lead wire 2 is buried in a direction corresponding to the longitudinal axis of the solid pole 1. The negative electrode 8 is formed on the outer surface of the solid pole 1 and the surface of the lead wire 2 is coated with the sealing agent 3 to form a solid electrode 4. The solid electrode 4 is tightly covered, wrapped or encased by the solid electrolyte 5 to press-mold it into a circular plate or small cylinder and the electrodes 6 and 7 are thus formed.

The positive electrode 6 is provided on the periphery of the side wall and the whole bottom surface of the oxygen sensor element A and the ⊔-shaped recess is formed on one portion of the surface of the positive electrode 6 provided on the periphery of the side wall. The negative auxiliary electrode 7 is provided in the form of a long band extending over the upper surface and the side wall of the element so that one end of the negative auxiliary electrode 7 is connected to the end of the lead wire 2 and the other end thereof is inserted into the recess of the positive electrode 6 as shown in FIG. 2.

However, as regards the electrodes to be formed on the surface of the solid electrolyte 5, it is sufficient if the negative auxiliary electrode 7 is formed only at the area connecting to the lead wire 2 and the other remaining area is the positive electrode 6. Therefore, the areas in which the positive electrode 6 and the negative auxiliary electrode 7 are formed, need not necessarily be limited to the areas shown in FIG. 2.

As mentioned above, the direction in which the lead wire 2 is buried may be made in conformity with the longitudinal direction or axis of the circular plate-like oxygen sensor element or in a direction transverse to the longitudinal axis of the oxygen sensor element. Furthermore, the profile of the lead wire need not be restricted to that shown in FIG. 2. It may be linear.

The ceramic insulator 9 to connect the oxygen sensor element A as constituted above will now be described with reference to FIGS. 3a, 3b, 3c, 4a, 4b, 4c, 4d and 4e.

FIG. 3a is a top plan view of the ceramic insulator 9, FIG. 3b is a front elevational view thereof, and FIG. 3c is a bottom plan view thereof. As shown in those Figs., a ring 9b is inserted into and bonded to the insulator 9 used with the present invention for housing within a holder. The ring 9b (FIG. 3b) is positioned substantially midway along the elongated cyindrical body 9b of the insulator 9. Electroconductive zones 10, 10' are formed in parallel on the surface of the insulator 9.

The tip of the bottom of the insulator 9 forms a cylindrical recess 9d to which the circular oxygen sensor element A is connected. The inner diameter of the recess corresponds to the diameter of the circular plate-like sensor element A to be joined thereto.

The ceramic insulator 9 is made of an insulating material, such as $Al_2O_3$, $MgO.A_2O_3$ (spinel), forsterite, or mullite.

The electroconductive zones 10, 10' are made of Pt and these are formed on the surface of the insulator 9 by Pt paste baking or printing.

Next, one embodiment in which the circular plate-like oxygen sensor element A is joined to the insulator 9 will be described with reference to FIGS. 4a, 4b, 4c, 4d and 4e. FIGS. 4a and 4b are enlarged side views of the vicinity of the junction between the sensor element A and the insulator as viewed from the positive and negative auxiliary electrodes; and FIG. 4c is a bottom plan view thereof. FIG. 4d is a front elevational view of FIGS. 4a and 4b; and FIG. 4e is a bottom plan view thereof.

As shown in those Figs., the circular plate-like oxygen sensor element A is joined with the tip of the insulator 9 by a binding agent 11 in such a manner that the upper surface of the circular plate-like oxygen sensor element A is in contact with the tip recess 9d of the insulator 9 and the side wall of the sensor element A provided with the electrodes 6 and 7 is in contact with and extends in the same direction as the electroconductive zones 10, 10'. The insulator 9 and the sensor element A are joined together with the binding agent 11 so that the electroconductive zone 10 is connected to the negative auxiliary electrode 7 of the sensor element A, and the other electroconductive zone 10' is connected to the positive electrode 6.

As shown in FIGS. 4b, 4c, 4d and 4e, an elctroconductive material 10a, 10a', such as Pt paste, may be coated between the electroconductive zones 10, 10' and the electrodes 6, 7 of the sensor element A so as to ensure a tight joint therebetween.

The joint between the electroconductive zones 10, 10' and the negative auxiliary electrode 7 and the positive electrode 6 is effected by baking Pt-paste.

The oxygen sensor element A is inserted into the tip recess 9d of the insulator and adhered to the tip recess 9d by means of the bonding agent 11, for instance, under heating in the atmosphere of Ar including 2% of $H_2$ at 145° C. for 15 minutes. As the bonding agent 11, $SiO_2$-MgO-base, $CaO$-$Al_2O_3$-MgO-base, $SiO_2$-CaO-$Al_2O_3$-base, $SiO_2$-$Al_2O_3$-MgO-base, $TiO_2$-base bonding agent, forsterite-, steatite- bonding agent, etc. are desirable. $CaO$-$Al_2O_3$-MgO-base $SiO_2$-MgO-base bonding agent are most desirable and these bonding agents are employed in powder form.

The housing 14, the flange 15 and the protecting cover 17 which constitute the holder for the solid pole oxygen sensor according to the present invention are made of stainless steel.

The sensor element A is secured to the holder, for instance, by caulking while heated in the air at, say, 600° C. The metal packing 12 used is a stainless steel ring or a copper ring. The filler 13 used is graphite, asbestos or pirophilite, etc. Tyrophillite is preferable.

When a solid pole oxygen sensor according to the present invention is set in the path of the exhaust from an automotive engine, the exhaust gas flowing along said path passes through the holes 18 of the protective cover 17 and comes into contact with the oxygen sensor element A, whereby a differential partial pressure developing between the equilibrium oxygen partial pressure $P_{o2}$ of the solid pole 1 and the oxygen partial pressure $P'_{o2}$ of the exhaust gas to be measured causes an electromotive force of the formula:

$$E = \frac{RT}{nF} \ln \frac{P'_{o2}}{P_{o2}} \quad \text{(Nernst formula)}$$

wherein
R: gas constant
T: absolute temperature
F: Faraday constant
Measurement of this electromotive force gives the oxygen concentration in the area to be measured.

The performance of the sensor element can be evaluated by He-leak test, the conductivity test, the autoclave method, the response test and appearance test.

HE-LEAK TEST

Figure 5:
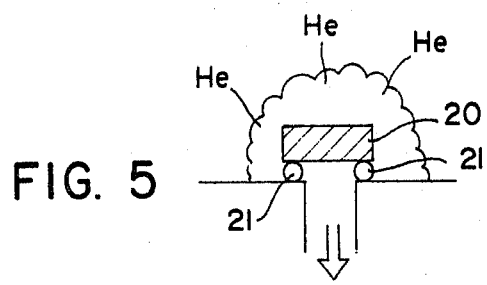
FIG. 5 is a diagram showing the He-leak test.

A specimen (sensor element) 20 is placed on O-rings (silicone rubber+silicone grease) 21, 21 is indicated in FIG. 5 and He-gas is blasted around them. In this state, air is sucked in the direction of the arrow shown in FIG. 5 and the He-concentration in the gas sucked is analyzed by a He-detector (not shown) for evaluation of the gas tightness of the element itself.

AUTOCLAVE METHOD

Figure 6:
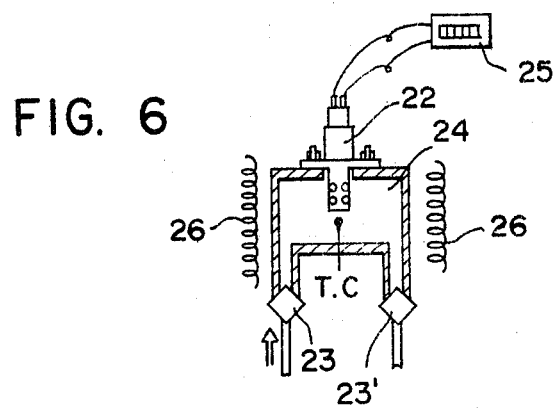
FIG. 6 is a diagram showing the autoclave method.

As indicated in FIG. 6, a solid pole oxygen sensor 22 assembled with the sensor element A according to the present invention is set at the center of a tube 24 with both ends closed by the electro-magnetic valves 23, 23', and a DC voltmeter 25 is connected to the sensor 22. Heaters 26 are installed around the tube 24. The atmosphere in the tube 24 is held at about 500° C. by the heater 26, while the air is pressurized to, say, 5 Kg/cm$^2$, by one of the valves 23. A change in the electromotive force developed thereby is measured by the DC voltmeter 25. Normally, the oxygen partial pressure difference rises with pressurization, causing a higher electromotive force, but the electromotive force will drop when the sealing is poor and the deterioration advances.

RESPONSE TEST

Figure 7:
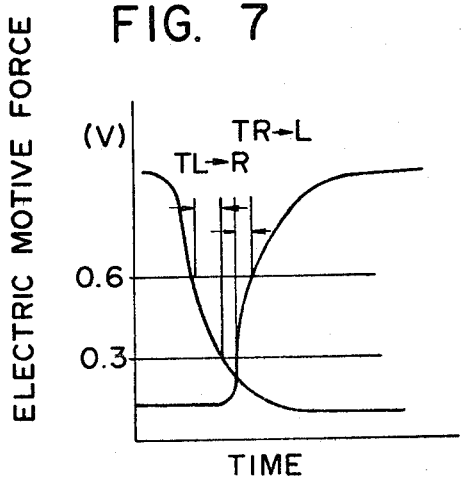
FIG. 7 is a graph illustrating the response characteristic of the oxygen sensor.

FIG. 7 is a diagram illustrating the response characteristic of the solid pole oxygen sensor as the oxygen concentration in the exhaust gas changes. Under rich→lean (R→L) or lean→rich (L→R) of the gasoline burning conditions, the electromotive force changes from 0.3 V to 0.6 V or vice versa. The time taken for this change is set as T(R→L), T(L→R). As deterioration starts after long service, T(R→L), T(L→R) become slow. The best dcondition is that both T(R→L) and T(L→R) are fast and the change is negligible before and after long service.

TEST EXAMPLE 1—LEAD WIRE DIAMETER AND RH ADDITION

Using lead wires of Pt and Pt/Rh, their performances depending on the diameter (mmφ) of lead wires and the Rh addition amount (% by weight) were investigated, the results are summarized in Table 1 and 2. The molding pressure thereby was set at 1200 Kg/cm$^2$.

TABLE 1

| Wire diameter | | | | |
|---|---|---|---|---|
| Wire diameter (mmφ) | 0.05 | 0.1 | 0.2 | 0.3 |
| Pt | Δ*1 | ○ | ○ | Δ*2 |

TABLE 2

| Conent of Rh added (% by weight) | Content of Rh added | | | | |
|---|---|---|---|---|---|
| Wire diameter | 10 | 15 | 20 | 25 | 35 | 40 |
| 0.1 mmφ | Δ*3 | ○ | ○ | ○ | Δ*4 | X |

The ratings in the above tables are as follows:
○ good
Δ marginally usable
X unfit for use
*1 no snapping of wire, but heat resistance poor
*2 Pt wire and solid electrolyte incompatible; sinterability of wire-surrounding solid electrolyte inferior
*3 wire flexibility reduced resulting in poor moldability
*4 wire hardness increased and elasticity decreased, making the wire unfit for use

TEST EXAMPLE 2—PRESENCE OF ELECTROCONDUCTIVE PASTE

Performance of an element (I) applied with electroconductive paste and a element (II) applied with no paste at start of use and after long service (*5) were evaluated by the response test, He-leak test, and autoclave method (air pressurization), the results being summarized in Table 3.

TABLE 3

| | Presence of electroconductive paste | | | | | |
|---|---|---|---|---|---|---|
| | Responce | | He-leak | | Auto clave | |
| Items Element | Start | After *5 long service | Start | After *5 long service | Start | After *5 long service |
| I | ○ | ○ | ○ | ○ | ○ | ○ |
| II | ○ | X | ○ | X | ○ | X | where *5 durability test condition = 10 mode run patterns × 200 hours

TEST EXAMPLE 3—MOLDING PRESSURE

The durability of molded products obtained under different molding pressures of Table 4 was evaluated after firing by the appearance test, response test, He-leak test and autoclave method to measure the effect of the molding pressure, the results are summarized in Table 4.

TABLE 4

| | Effect of molding pressure | | | | | | | |
|---|---|---|---|---|---|---|---|---|
| Item | Appearance after firing | | Response | | He-leak | | Autoclave | |
| Pressure (Kg/cm$^2$) | Start | After long service | Start | After long service | Start | After long service | Start | After long service |
| 600 | ○ | Δ | Δ | X | Δ | X | Δ | X |
| 1000 | ○ | ○ | ○ | Δ | ○ | Δ | ○ | Δ |
| 1200 | ○ | ○ | ○ | ○ | ○ | ○ | ○ | ○ |
| 1500 | ○ | ○ | ○ | ○ | ○ | ○ | ○ | ○ |
| 2000 | ○ | ○ | ○ | ○ | ○ | ○ | ○ | ○ |
| 2200 | X | X | X | X | X | X | X | X | where
○ good
X unfit for use (with deterioration)
Δ occasionally rejected

It is evident from the above that the oxygen sensor according to the present invention, having its solid pole wrapped in a solid electrolyte and being low-temperature fired after molded, needs no calcining or high-temperature firing of the solid electrolyte.

The structure of the invention can be miniaturized, because an electroconductive sealing agent is applied to the lead wire buried in the solid pole.

Furthermore, since the circular plate-like sensor element is secured to the tip of the insulator in such a manner that the tip of the insulator is in contact with the upper surface of the element, the resulting oxygen sensor is simple in structure, and the element and the insulator are very tightly joined. Therefore, the present invention is advantageous because the steps of the manufacturing process are simplified and the oxygen sensor of the present invention is durable for long usage.

What we claim is:

1. A solid pole oxygen sensor comprising:
    a substantially cylindrical ceramic insulator having electroconductive zones on the outer surface thereof;
    an adhesive;
    a circular plate-shaped oxygen sensor element having a circular surface joined by said adhesive to one end of the insulator and comprising:
        a solid pole;
        a lead wire, one end of which is buried in the solid pole, said lead wire being made of Pt or Pt-Rh; and
        a solid electrolyte in which the solid pole is encased;
    first and second electrode means connecting different areas of said electrolyte to different electroconductive zones of said insulator; and
    the end of the insulator is in contact with the circular surface on one end of the sensor element.

2. A solid pole oxygen sensor as claimed in claim 1, wherein the solid pole is made of Co/CoO, V/VO or Fe/FeO and other additives comprising an anti-sinter agent; and an activating agent.

3. A solid pole oxygen sensor as claimed im claim 1, wherein the lead wire is made of Pt or Pt-Rh and has a diameter in the range of 0.05–0.5 mm$\phi$.

4. A solid pole oxygen sensor as claimed in claim 1, further comprising an electroconductive sealing paste on the surface of the lead wire and the outer surface of the solid pole.

5. A solid pole oxygen sensor as claimed in claim 4, wherein the entire surface of the lead wire exterior of the solid pole is coated with the electroconductive paste.

6. A solid pole oxygen sensor as claimed in claim 1, wherein the end of the lead wire buried in the solid pole is bent in a substantially circular configuration.

7. A solid pole oxygen sensor as claimed in claim 1, wherein the adhesive is selected from the group consisting of $CaO\text{-}Al_2O_3\text{-}MgO$, $SiO_2\text{-}CaO\text{-}Al_2O_3$, $SiO_2\text{-}MgO$ or $TiO_2\text{-}Bao$.

8. A solid pole oxygen sensor comprising:
    a substantially cylindrical ceramic insulator having two longitudinally extending electroconductive zones spaced from each other thereon, means defining a recess in one end of the insulator;
    an adhesive;
    a disc-shaped oxygen sensor element extending into the recess from the one end of the insulator and joined by said adhesive to the one end of the insulator, said element having positive and negative electrodes formed on the circular surface thereof and comprising;
        a solid pole;
        a lead wire, one end of which is buried in the solid pole, said lead wire being made of Pt or Pt-Rh; and
        a solid electrolyte in which the solid pole is encased; and
    the end of the insulator is in contact with the circular upper surface of the sensor element with the electroconductive zones in contact with the positive and negative electrodes.

9. A solid pole oxygen sensor comprising;
    a substantially cylindrical ceramic insulator having two longitudinally extending electroconductive zones spaced from each other thereon;
    an adhesive;
    a disc-shaped oxygen sensor element joined by said adhesive to one end of the insulator, said element having positive and negative electrodes formed on the circular surface on one end thereof and the cylindrical sidewall thereof and comprising;
        a solid pole;
        a lead wire, one end of which is buried in the solid pole, said lead wire being made of Pt or Pt-Rh; and
        a solid electrolyte in which the solid pole is encased; and
    the end of the insulator is in contact with the periphery of the sensor element with the electroconductive zones in contact with the positive and negative electrodes.

10. A solid pole oxygen sensor as claimed in claim 9, wherein:
    said recess is in contact with and adhesively secured to both the circular surface and the cylindrical sidewall of the oxygen sensor element.

11. The solid pole oxygen sensor of claim 1, wherein one of said electrodes comprises a metallic strip connected at one end to an area of said electrolyte adjacent said lead wire, the remaining end extending away from said area to a first electroconductive zone of said insultaor, the remaining of said electrodes being connected from an area away from said lead wire to a second electroconductive zone of said insulator.

* * * * *